(12) United States Patent
Hsieh et al.

(10) Patent No.: US 7,108,678 B2
(45) Date of Patent: Sep. 19, 2006

(54) CAPTIVE COVER FOR A HYPODERMIC NEEDLE OF AN INTRAVENOUS (IV) TUBE ASSEMBLY

(75) Inventors: Hsin-Po Hsieh, Chian-Hwa Hsien (TW); Chi-Zer Ho, Taipei (TW); Shih-Chun Wang, Chia-Yi (TW)

(73) Assignee: Biotop Holding Co., Ltd., Grand Cayman (KY)

( * ) Notice: Subject to any disclaimer, the term of this patent is extended or adjusted under 35 U.S.C. 154(b) by 360 days.

(21) Appl. No.: 10/749,838

(22) Filed: Dec. 31, 2003

(65) Prior Publication Data

US 2005/0148930 A1 Jul. 7, 2005

(51) Int. Cl.
*A61M 5/00* (2006.01)

(52) U.S. Cl. .................. 604/110; 604/263; 128/919

(58) Field of Classification Search ............ 604/93.01, 604/110, 187, 192, 263–264; 128/919
See application file for complete search history.

(56) References Cited

U.S. PATENT DOCUMENTS

| | | | | |
|---|---|---|---|---|
| 4,664,259 A | * | 5/1987 | Landis | 206/365 |
| 4,973,315 A | * | 11/1990 | Sincock | 604/192 |
| 5,017,189 A | * | 5/1991 | Boumendil | 604/192 |
| 5,055,102 A | * | 10/1991 | Sitnik | 604/192 |
| 6,409,705 B1 | * | 6/2002 | Kondo | 604/192 |
| 6,520,938 B1 | * | 2/2003 | Funderburk et al. | 604/164.08 |
| 6,582,397 B1 | * | 6/2003 | Alesi et al. | 604/110 |
| 6,719,737 B1 | * | 4/2004 | Kobayashi | 604/263 |

* cited by examiner

*Primary Examiner*—LoAn H. Thanh
(74) *Attorney, Agent, or Firm*—Alan D. Kamrath; Nikolai & Mersereau, P.A.

(57) ABSTRACT

A captive cover for a hypodermic needle of an IV tube assembly has an elongated body connected to an element of the IV tube assembly. The elongated body is hollow and has a proximal opening, a closed distal end, a chamber, at least one locking tab and one or more optional connectors. The hypodermic needle of the IV tube assembly can be inserted through the proximal opening into the chamber. A flange on the hypodermic needle of the IV tube assembly is held in the captive cover by the locking tab. Since the hypodermic needle of the IV tube assembly only passes through the locking tab of the elongated body, the hypodermic needle of the IV tube assembly can be conveniently inserted into the elongated body. The captive cover can accommodate an ordinary hypodermic needle and has a simple structure.

3 Claims, 8 Drawing Sheets

CAPTIVE COVER FOR A HYPODERMIC NEEDLE OF AN INTRAVENOUS (IV) TUBE ASSEMBLY

BACKGROUND OF THE INVENTION

1. Field of the Invention

The present invention relates to a safety device, and more particularly to a captive cover for a hypodermic needle of an intravenous (IV) tube assembly.

2. Description of Related Art

Since some patients cannot ingest nutrients or medicine orally, nutrients or medicine must be administered intravenously from an IV solution container. A conventional IV solution container must have an IV tube assembly to connect the IV solution container to a patient.

The IV tube assembly comprises a container needle, an upper IV tube, a lower IV tube, an injection joint, a flow control apparatus and a hypodermic needle. The upper IV tube and the lower IV tube respectively have upper ends and lower ends. The container needle is connected to the upper end of the upper IV tube and is inserted into the IV solution container. The injection joint comprises an intermediate container and a lid. The intermediate container has a bottom, an open top and a discharge outlet. The discharge outlet is formed on the bottom of the intermediate container and is connected to the upper end of the lower IV tube. The lid is mounted securely on the open top of the intermediate container. The lower end of the upper IV tube is connected to the lid. The flow control apparatus is mounted around the lower IV tube to control how quickly an IV solution is administered to a patient. The hypodermic needle is connected to the lower end of the lower IV tube and is inserted into a patient's vein so the IV solution can be administered to a patient.

A conventional hypodermic needle has a cover to protect the hypodermic needle. The cover is removed when the IV is administered to a patient and replaced on the hypodermic needle when the administration of an IV solution to the patient is complete. However, two problems exist with the small conventional cover. First, the cover is easily lost between the time it is removed from the needle and the time it needs to be replaced on the needle. This makes the contaminated IV hypodermic needle a personnel hazard during the disposal process. Second, the cover is small, and medical personnel are subject to puncture injuries from the contaminated needle during the process of replacing the cover over the hypodermic needle.

Figure 7:
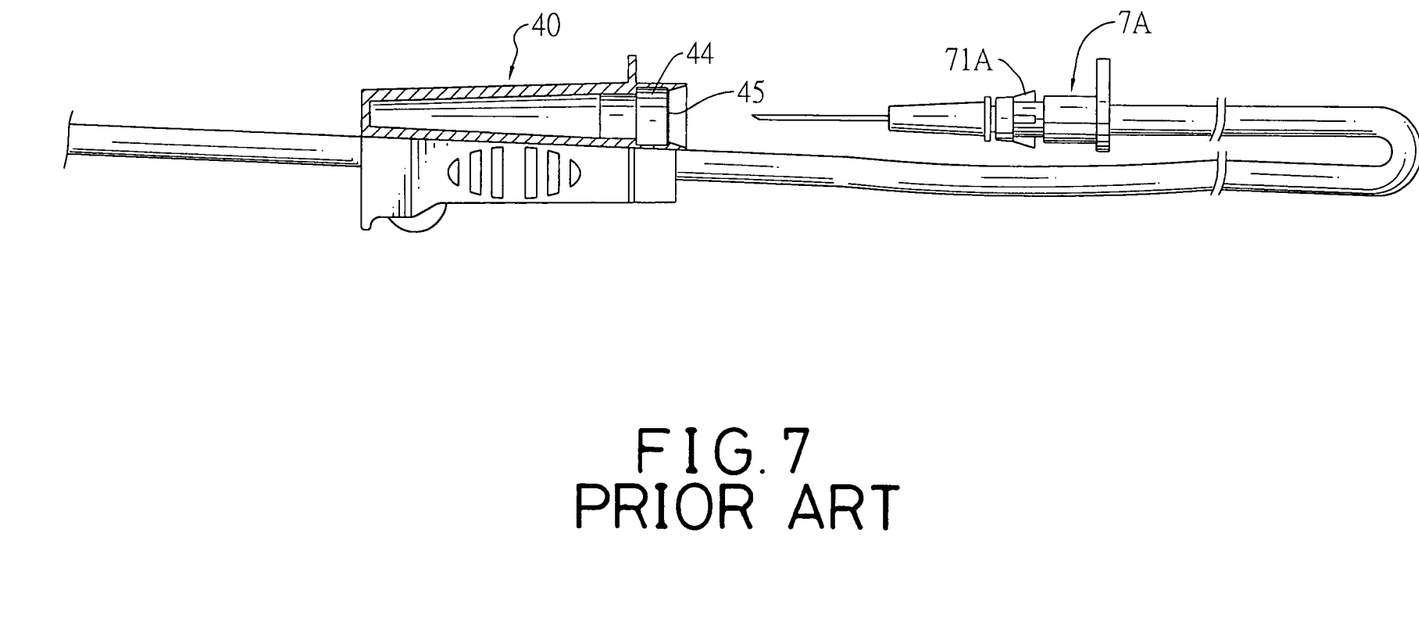
FIG. 7 is a cross sectional side plan view of a conventional captive cover in accordance with the prior art showing the hypodermic needle before being inserted into the captive cover.
Figure 8:
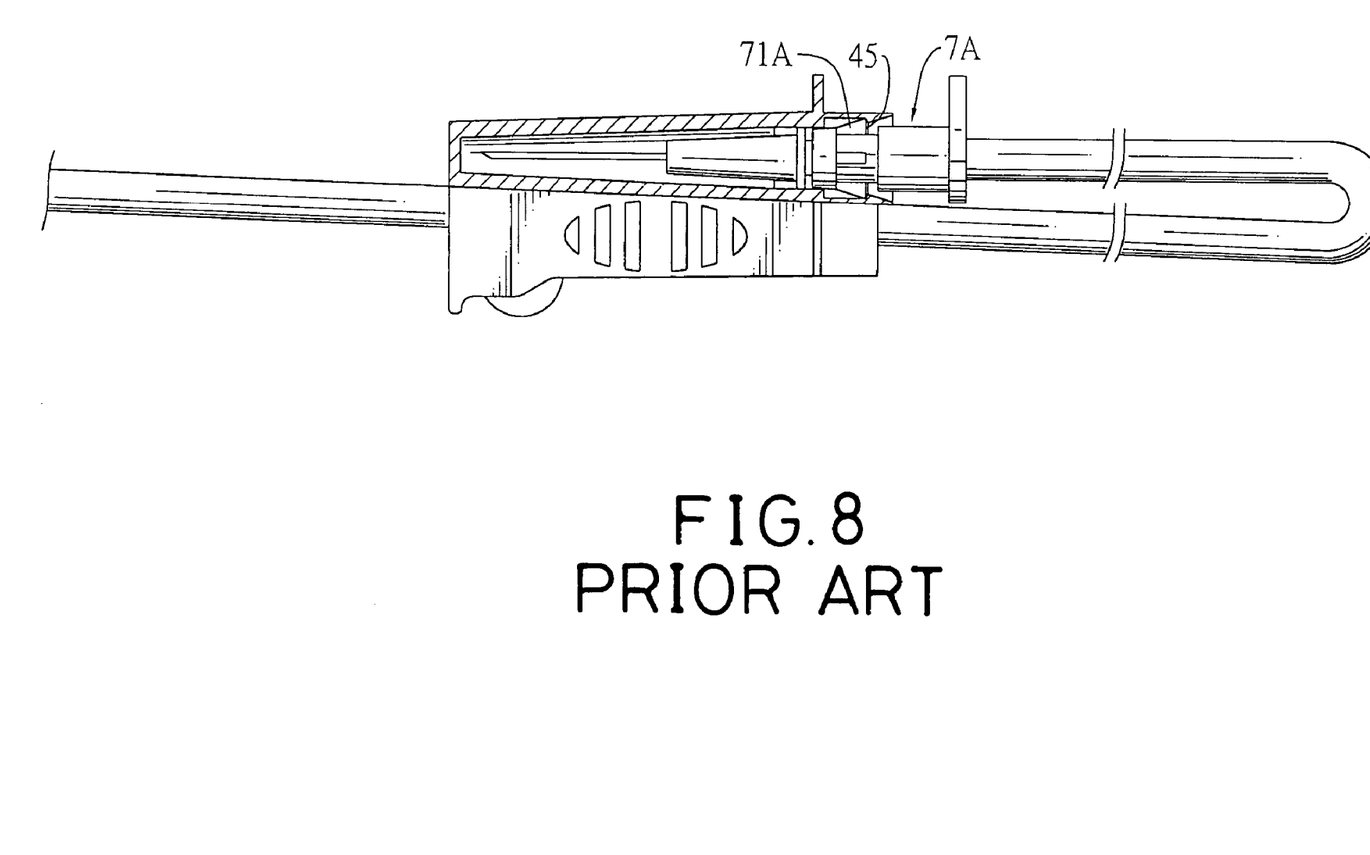
FIG. 8 is a cross sectional side plan view of the conventional captive cover in FIG. 7 with the hypodermic needle in the captive cover.

With reference to FIGS. 7 and 8, a captive cover (40) disclosed in Taiwan Patent No. 90221792 obviates the problem with loosing the cover, is formed integrally with and extends from a flow control apparatus (not numbered) and comprises a chamber (44) and an annular rib (45). The chamber (44) has a closed distal end (not numbered) and an open proximal end (not numbered). The annular rib (45) extends radially inward from the open proximal end of the chamber (44). A hypodermic needle (7A) of an IV tube assembly has multiple resilient locking tabs (71A) formed around the hypodermic needle (7A) of the IV tube assembly. The hypodermic needle (7A) can be pushed into the chamber (44) of the captive cover (40), which compresses the resilient locking tabs (71A) until the locking tabs (71A) pass the annular rib (45) that securely holds the hypodermic needle (7A) in the chamber (44) of the captive cover (40). The captive cover (40) can prevent personnel injuries from the contaminated hypodermic needle (7A) during the disposal process.

However, the hypodermic needle (7A) must be compatible with the conventional captive cover (40) to provide the safety effect. The conventional captive cover (40) is not compatible with ordinary hypodermic needles for the IV tube assembly. Modification of conventional hypodermic needles to obtain hypodermic needles (7A) compatible with the captive cover (40) will increase the cost of the manufacturing. Furthermore, a significant amount of pressure is required to push the locking tab (71A) of the hypodermic needle (7A) through the annular rib (45) of the conventional captive cover (40). Since the conventional captive cover (40) is suspended in the air with the IV tube assembly, pressing the hypodermic needle (7A) into the captive cover (40) that will shake and possibly dislodge the entire IV tube assembly.

SUMMARY OF THE INVENTION

The main objective of the present invention is to provide a captive cover for a hypodermic needle of an IV tube assembly that has a simple structure and allows the hypodermic needle of the IV tube assembly to be conveniently inserted into the captive cover.

To achieve the objective, a captive cover is provided for a hypodermic needle of an IV tube assembly, which has a needle and a needle hub, and comprises an elongated body. The elongated body is formed or mounted on an element of the IV tube assembly and has a proximal opening, a closed distal end, a chamber and at least one locking tab. The hypodermic needle of the IV tube assembly is inserted through the proximal opening into the chamber. The hub of the hypodermic needle is held in the chamber by the locking tab so the hypodermic needle cannot be pulled out of the captive cover. Since the hypodermic needle of the IV tube assembly only passes by the locking tab of the elongated body, the hypodermic needle of the IV tube assembly can be conveniently inserted into the elongated body. The captive cover compatible with ordinary conventional hypodermic needles, has a simple structure and costs less to manufacture than the conventional captive cover.

Further benefits and advantages of the present invention will become apparent after a careful reading of the detailed description with appropriate reference to the accompanying drawings.

DETAILED DESCRIPTION OF THE INVENTION

With reference to FIGS. 1, 3, 4 and 5, a captive cover in accordance with the present invention for a hypodermic needle of an intravenous (IV) tube assembly with multiple elements including a container needle, an upper tube, a lower tube, a flow control apparatus and a hypodermic needle comprises an elongated body (12, 12') attached longitudinally to an element of the IV tube assembly. The elongated body (12, 12') is hollow and has an outside surface (not numbered), a proximal opening (14, 14'), a closed distal end (not numbered), a chamber (13, 13'), at least one locking tab (16, 16') and one or more optional connectors (18). The proximal opening (14, 14') is tapered inward. The chamber (13, 13') is formed longitudinally in the elongated body (12, 12') between the proximal opening (14, 14') and the closed distal end, communicates with the tapered proximal opening (14, 14') and tapers slightly toward the closed distal end. The at least one locking tab (16, 16') is resilient, is formed in the outside surface near the proximal opening (14, 14') and protrudes into the chamber (13, 13') toward the distal end.

Figure 1:
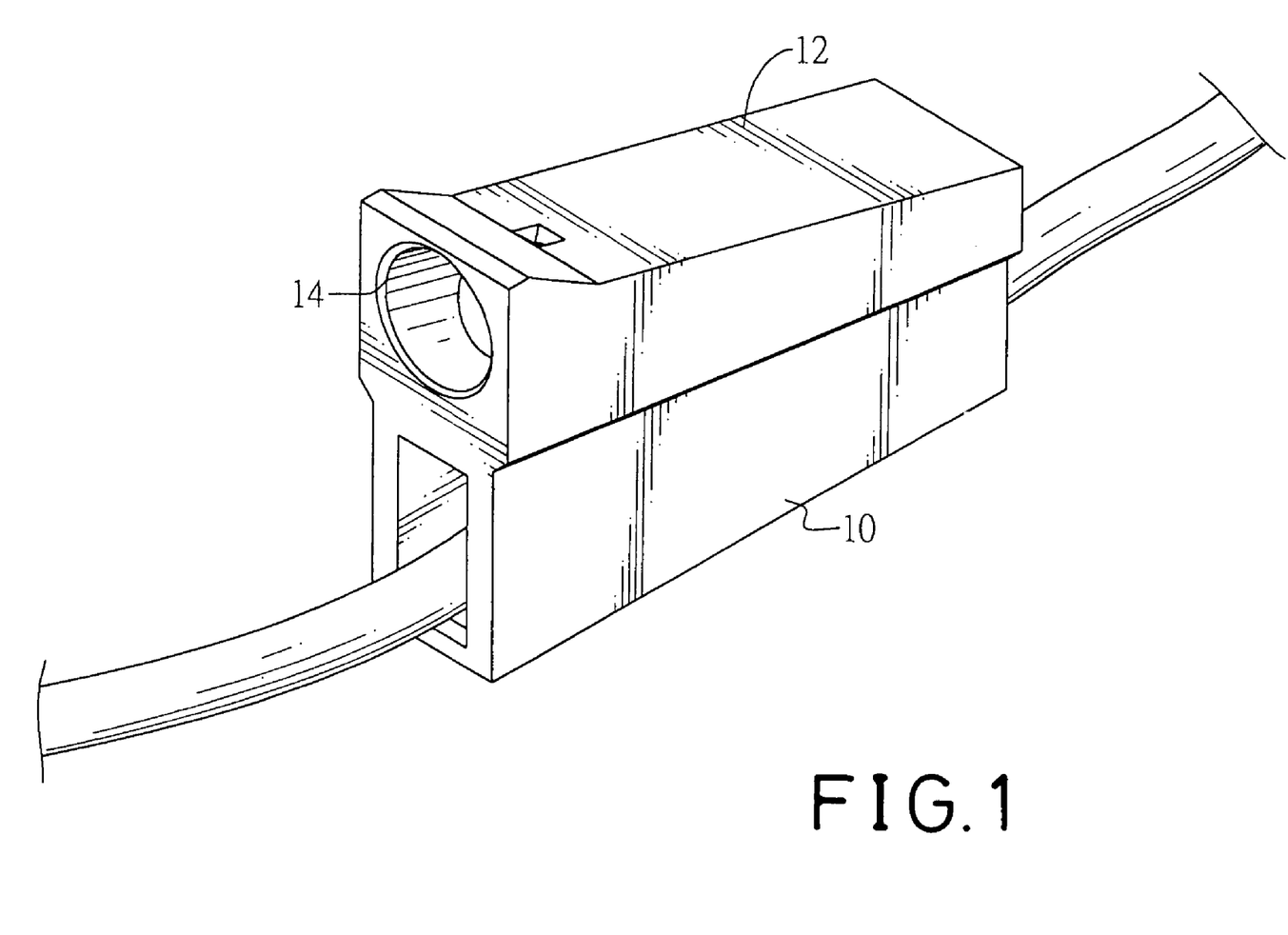
FIG. 1 is a perspective view of a first embodiment of a captive cover for a hypodermic needle of an IV tube assembly in accordance with the present invention.
Figure 2:
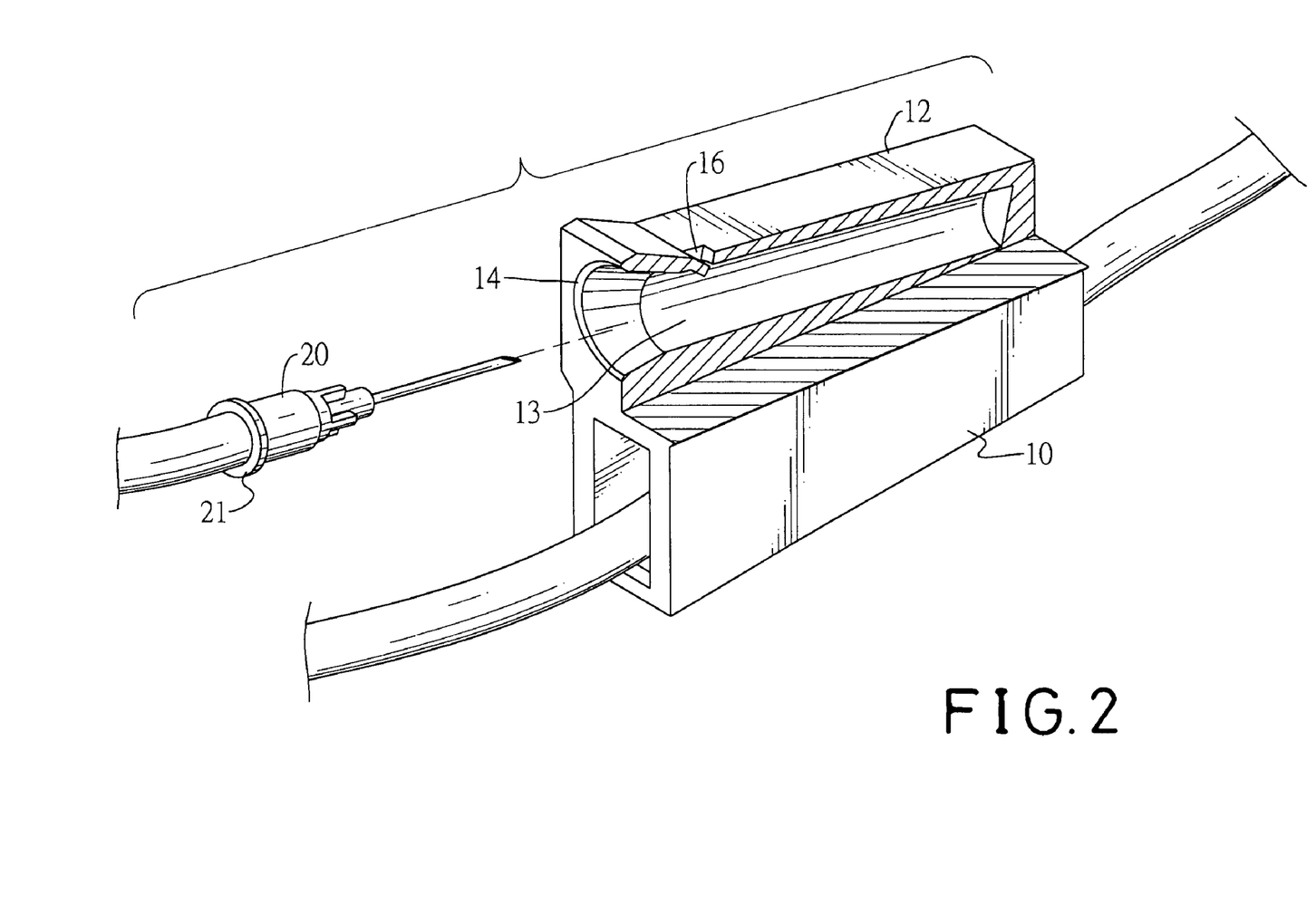
FIG. 2 is a cross sectional perspective view of the captive cover in FIG. 1 showing a hypodermic needle before being inserted in the captive cover.

With reference to FIGS. 1 and 2, a first embodiment of the captive cover for a hypodermic needle of an IV tube assembly in accordance with the present invention comprises an elongated body (12) formed longitudinally on an element of the IV tube assembly. The elongated body (12) extends from the element of the IV tube assembly. Preferably, the elongated body (12) is formed integrally with and extends from a flow control apparatus (10). In the embodiment described, the elongated body (12) has one locking tab (16).

Figure 4:
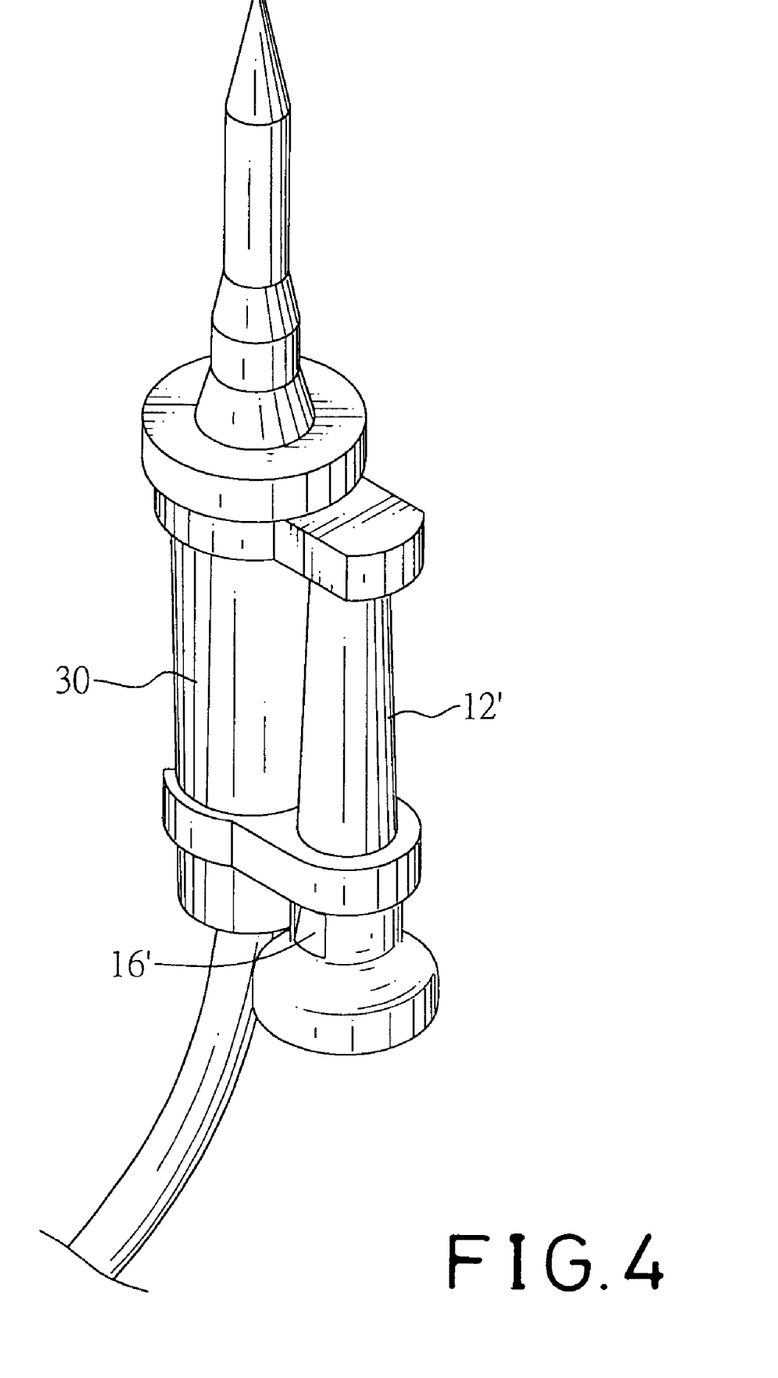
FIG. 4 is a perspective view of a second embodiment of a captive cover for a hypodermic needle of an IV tube assembly in accordance with the present invention.
Figure 5:
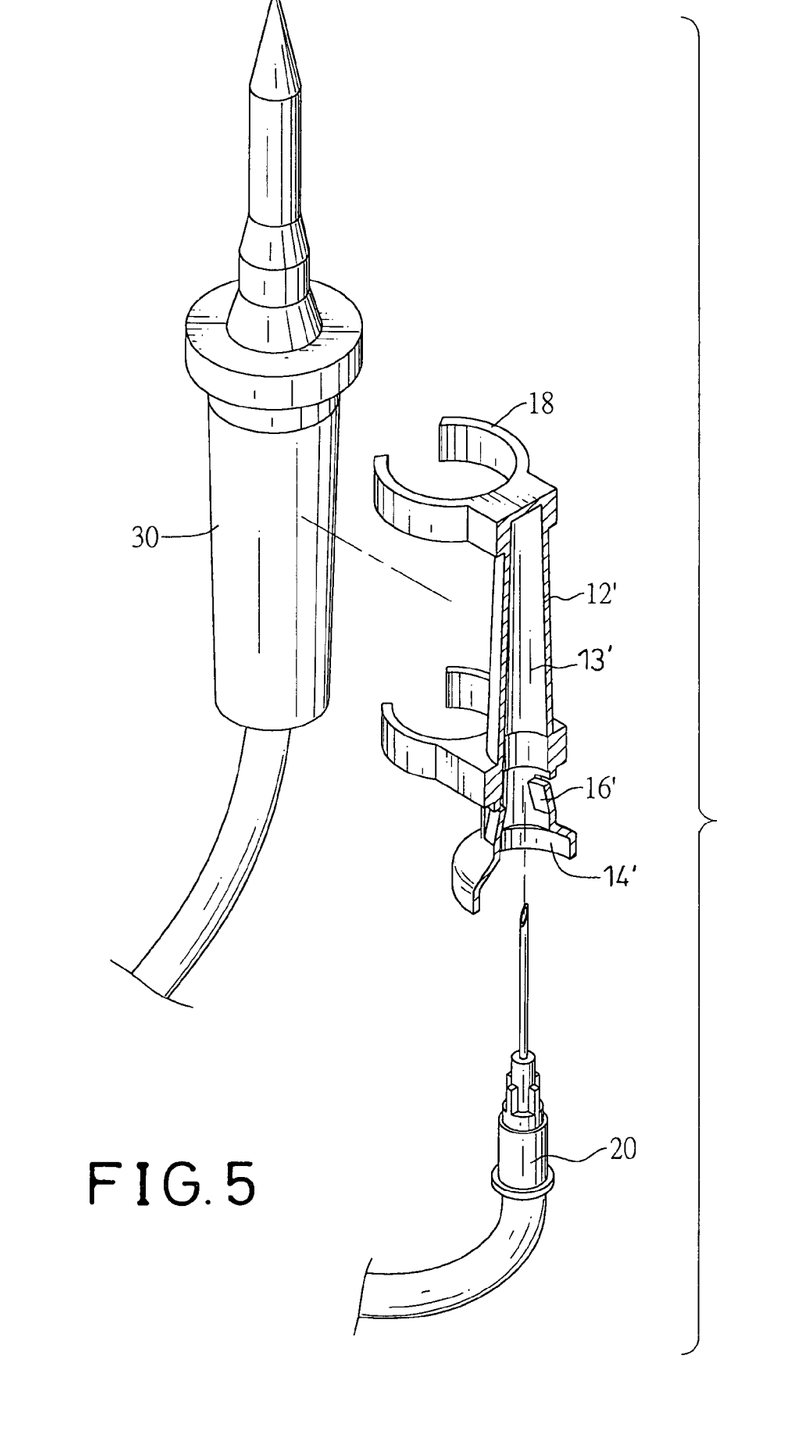
FIG. 5 is a cross sectional exploded perspective view of the captive cover in FIG. 4 showing the hypodermic needle before being inserted into the captive cover.
Figure 6:
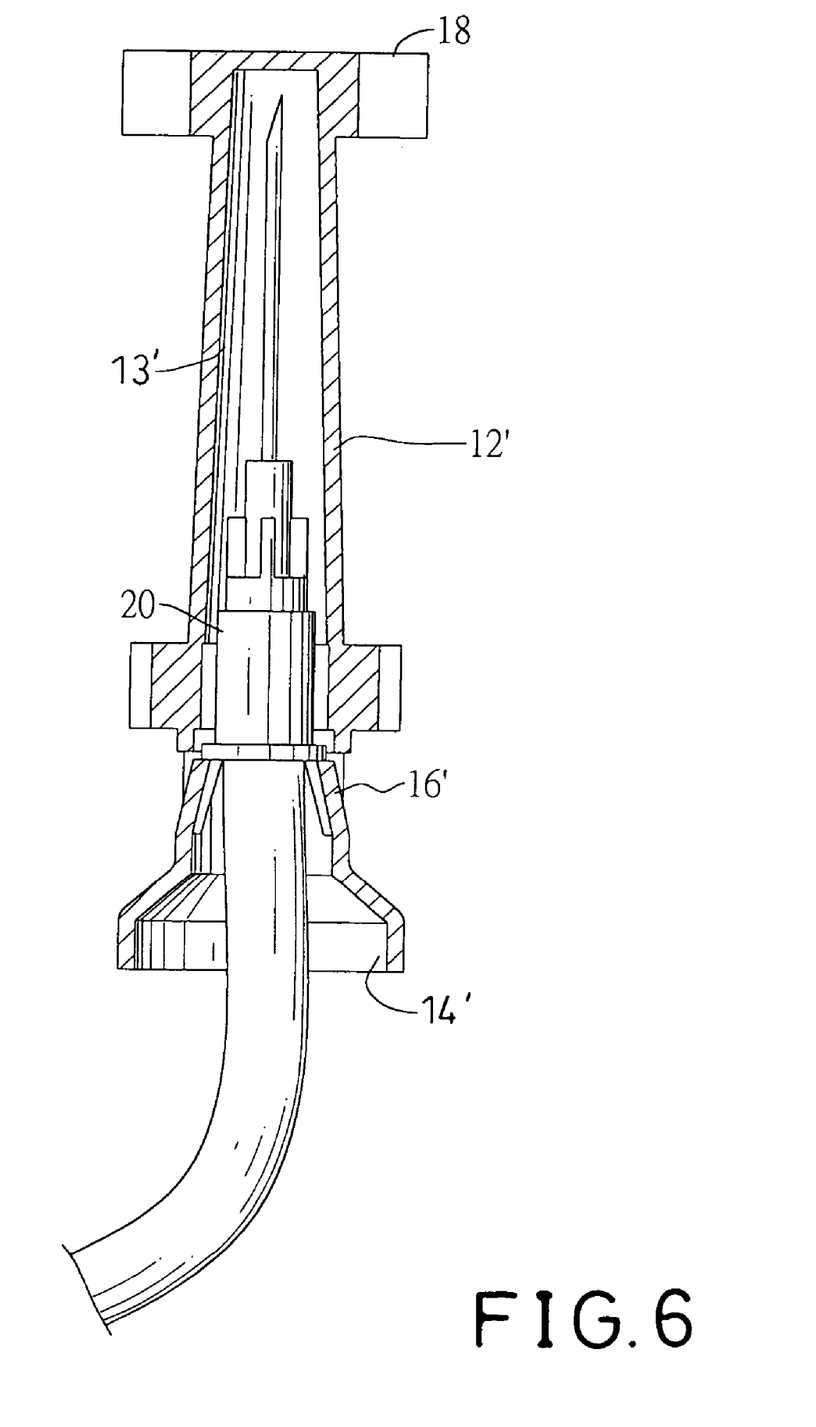
FIG. 6 is a cross sectional side plan view of the captive cover in FIG. 4 with the hypodermic needle in the captive cover.

With reference to FIGS. 4 to 6, a second embodiment of a captive cover for a hypodermic needle of an IV tube assembly in accordance with the present invention further comprises an elongated body (12') and at least one connector (18). In the second embodiment, the elongated body (12') has two locking tabs (16'). The at least one connector (18) is formed integrally with and extends radially from the elongated body (12'). Preferably, the captive cover has two connectors (18) formed integrally with and extending radially respectively from the distal end and near the proximal opening (14') of the elongated tube (12'). Preferably, the at least one connector (18) is a C-shaped resilient clip. The at least one connector (18) is connected to an element of the IV tube assembly. Preferably, the at least one connector (18) is connected to a container needle (30).

Figure 3:
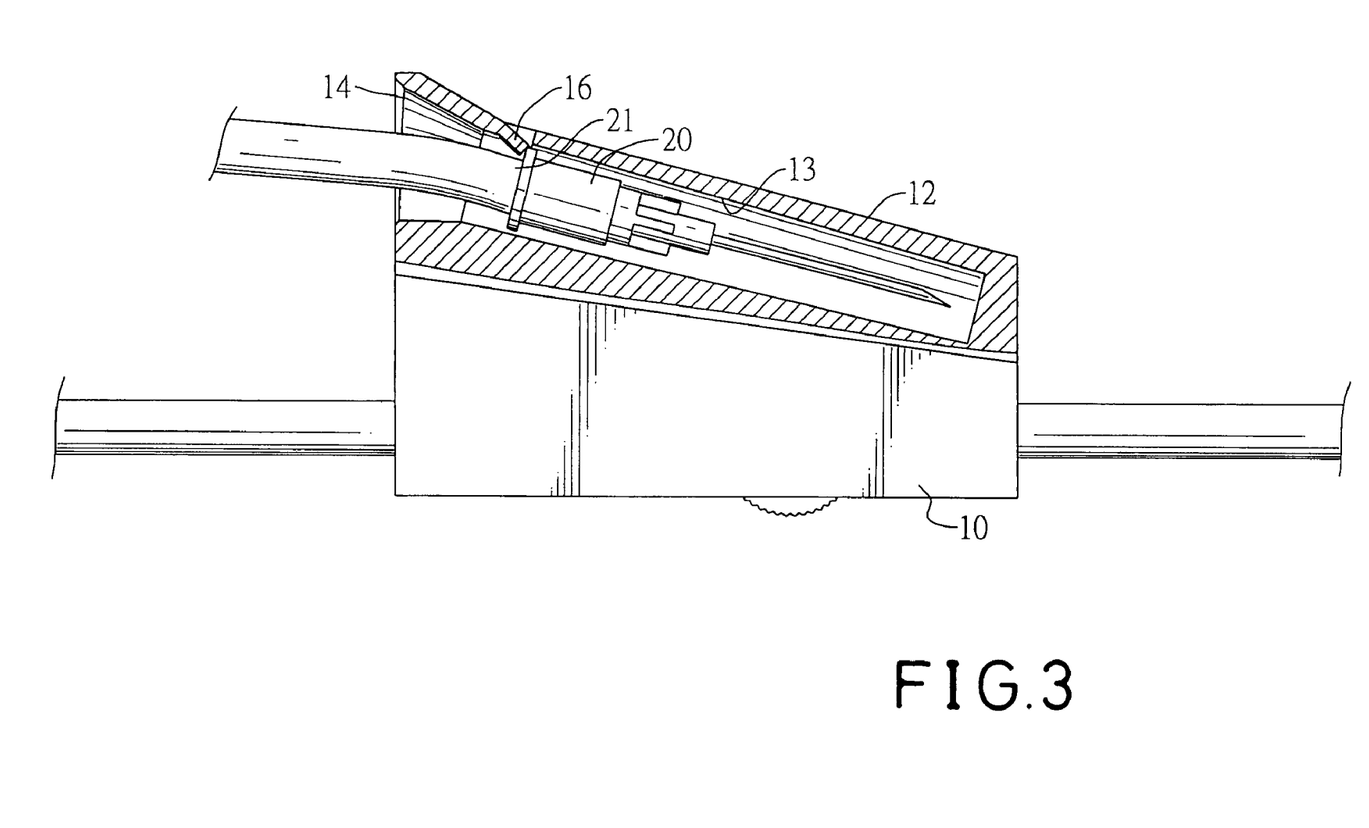
FIG. 3 is a cross sectional side plan view of the captive cover in FIG. 1 with the hypodermic needle in the captive cover.

With further reference to FIG. 3, a hypodermic needle of an IV tube assembly has a needle hub (20) and a needle (not numbered). The needle hub (20) has a proximal end (not numbered), a distal end (not numbered) and an annular flange (21). In both the first and second embodiments of the captive cover, the hypodermic needle of the IV tube assembly is inserted through the proximal opening (14, 14') and into the chamber (13, 13') of the elongated body (12, 12'), the annular flange (21) of the hypodermic needle (20) is held in the elongated body (12, 12') by the locking tab(s) (16, 16').

The captive cover for the hypodermic needle of the IV tube assembly as described is attached to an element of the IV tube assembly, and the hypodermic needle can be conveniently inserted into the captive cover. Since the hypodermic needle just passes through the one or more resilient locking tabs, the hypodermic needle do not need a significant amount of pressure to pass through the one or more locking tab. The captive cover can accommodate ordinary hypodermic needles, has a simple structure and is cheaper than the conventional captive cover.

Although the invention has been explained in relation to its preferred embodiment, many other possible modifications and variations can be made without departing from the spirit and scope of the invention as hereinafter claimed.

What is claimed is:

1. A captive cover for a hypodermic needle of an intravenous (IV) tube assembly with multiple elements including a container needle, an upper tube, a lower tube and a flow control apparatus, the captive cover comprising an elongated body adapted to be attached longitudinally to an element of the IV tube assembly, wherein
   the elongated body is hollow and has
      an outside surface;
      a proximal opening tapered inward;
      a closed distal end;
      a chamber formed longitudinally in the elongated body between the proximal opening and the closed distal end, communicating with the tapered proximal opening and tapering slightly toward the closed distal end;
      at least one resilient locking tab formed in the outside surface near the proximal opening and protruding into the chamber toward the distal end; and
      two connectors formed integrally with and extending radially from the outside of the elongated body respectively from the distal end and near the proximal opening of the elongated body to connect to an element of the IV tube assembly.

2. The captive cover as claimed in claim 1, wherein the elongated body has one locking tab.

3. The captive cover as claimed in claim 1, wherein each connector is a C-shaped clip.

* * * * *